(12) United States Patent
Steffen et al.

(10) Patent No.: US 11,692,984 B2
(45) Date of Patent: Jul. 4, 2023

(54) GAS CONCENTRATION MEASUREMENT WITH TEMPERATURE COMPENSATION

(71) Applicant: GEA Food Solutions Germany GmbH, Biedenkopf-Wallau (DE)

(72) Inventors: Andreas Steffen, Hatzfeld-Holzhausen (DE); Roland Jaindl, Großwilfersdorf (AT); Johannes Krottmaier, Hart bei Graz (AT)

(73) Assignee: GEA Food Solutions Germany GmbH, Biedenkopf-Wallau (DE)

( * ) Notice: Subject to any disclaimer, the term of this patent is extended or adjusted under 35 U.S.C. 154(b) by 0 days.

(21) Appl. No.: 16/610,149

(22) PCT Filed: May 3, 2018

(86) PCT No.: PCT/EP2018/061369
§ 371 (c)(1),
(2) Date: Nov. 1, 2019

(87) PCT Pub. No.: WO2018/202784
PCT Pub. Date: Nov. 8, 2018

(65) Prior Publication Data
US 2021/0072205 A1    Mar. 11, 2021

(30) Foreign Application Priority Data
May 4, 2017    (DE) .................. 10 2017 207 492.2

(51) Int. Cl.
*G01N 31/22*    (2006.01)
*G01N 21/78*    (2006.01)
(Continued)

(52) U.S. Cl.
CPC ....... *G01N 31/225* (2013.01); *G01N 21/6408* (2013.01); *G01N 21/783* (2013.01); *G01N 33/0036* (2013.01)

(58) Field of Classification Search
CPC ............. G01N 21/6408; G01N 21/643; G01N 21/783; G01N 31/225; G01N 33/0036;
(Continued)

(56) References Cited

U.S. PATENT DOCUMENTS

2007/0003743 A1*  1/2007  Asano ................... B82Y 30/00
                                                           428/201
2007/0212789 A1*  9/2007  Havens .............. G01N 21/6408
                                                           436/138
(Continued)

FOREIGN PATENT DOCUMENTS

WO    2004/010094 A1    1/2004

OTHER PUBLICATIONS

European Examination Report dated Aug. 28, 2020, for European Application EP18722495.1.
(Continued)

*Primary Examiner* — Matthew D Krcha
*Assistant Examiner* — Austin Q Le
(74) *Attorney, Agent, or Firm* — The Dobrusin Law Firm, P.C.

(57) ABSTRACT

The invention relates to a method for measuring the concentration of a gas component in an atmosphere of a packaging which is made from a plastic film and which comprises a gas concentration indicator substance on the side of the plastic film facing the atmosphere.

15 Claims, 4 Drawing Sheets

(51) Int. Cl.
*G01N 21/64* (2006.01)
*G01N 33/00* (2006.01)

(58) Field of Classification Search
CPC .................. G01N 33/02; G01N 33/12; G01N 2021/6439; G01N 2021/6441; G01N 2033/009; G01M 3/226; G01M 3/38; G01J 2009/008; Y10T 436/20; Y10T 436/209163
See application file for complete search history.

(56) References Cited

U.S. PATENT DOCUMENTS

| | | | | |
|---|---|---|---|---|
| 2007/0212792 | A1* | 9/2007 | Havens | G01M 3/226 436/172 |
| 2010/0293899 | A1* | 11/2010 | Boekstegers | B65D 81/2076 53/507 |
| 2011/0050431 | A1* | 3/2011 | Hood | G01N 33/14 340/603 |
| 2013/0177480 | A1 | 7/2013 | Fernandes et al. | |
| 2019/0041338 | A1* | 2/2019 | Tobias | G01N 31/223 |

OTHER PUBLICATIONS

International Search Report and Written Opinion for International Application PCT/EP2018/061369, dated Aug. 8, 2018.
International Preliminary Report on Patentability for International Application No. PCT/EP2018/061369, dated Aug. 13, 2019.
Hannemann Birgit et al: Influence of temperature of the luminescence decay time on the behavior of a luminescence quenching oxygen sensor, Advances in Fluorescence Sensing Technology II; dated May 8, 1995.
XP055071464—Michaela Quaranta—Indicators for optical oxygen sensors (2012).

* cited by examiner

Figure 8: The temperature-dependent calibration parameters $\tau$, $K_{SV}$, f $\tau$ = TAU measured $\tau_0$ = TAU 0 = calibration parameter at 0% oxygen content in the package

GAS CONCENTRATION MEASUREMENT WITH TEMPERATURE COMPENSATION

The present invention relates to a method for measuring the concentration of a gas component in the atmosphere of a package, from a plastic film and/or a paper film/cardboard and/or a metal film or combinations thereof, and having a gas concentration indicator substance on the side of the plastic film facing the atmosphere.

Food packages increase the stability of foods but only if the packages are impermeable and/or if the atmosphere in the package has a certain composition, in particular when the oxygen concentration in the atmosphere in the package is below a certain level. Methods of determining the oxygen concentration are known from the prior art, for example, from WO 2015172166 A1, but these methods are either comparatively inaccurate and/or slow and time consuming because they utilize comparatively slow methods of detecting the intensity of emitted light in investigating fast packaging processes or methods which involve damage to the package.

The object of the present invention is therefore to make available a method for measuring the gas concentration of the atmosphere in a package, such that the method does not have the disadvantages of the prior art.

This object is achieved with a method for measuring the gas concentration in the atmosphere of a package, which is preferably manufactured from a plastic film and/or a paper film/cardboard and/or a metal film or combinations thereof, and which has a gas concentration indicator substance on the side of the packaging material, in particular the plastic film, facing the atmosphere, such that the gas concentration indicator substance is exposed to an electromagnetic radiation which has a certain wavelength and emits light, preferably of a different wavelength, and the gas concentration is determined on the basis of the decay curve of the light thereby emitted.

The present invention relates to a method for measuring the gas concentration in the atmosphere of a package. The package contains packaging material, in particular a food or some other sensitive packaging material, for example, a sterile material. The package itself consists of one or more plastic films and/or paper film/cardboard and/or metal film or combinations thereof, which may also be embodied or extruded or cast in multiple layers and consisting of different materials. The package preferably has a deep-drawn package recess in particular, which is filled with the packaging material and is then sealed with a cover, in particular a cover film. The cover film is sealed to the package recess. Before sealing, a gas exchange is preferably performed in the package recess. To do so, air is first evacuated out of the package recess, thereby creating a vacuum in the package recess. Then the replacement gas, in particular an inert gas, such as $CO_2$ and/or $N_2$, is preferably introduced into the package recess, thereby lowering the oxygen concentration in the package recess so that, for example, the stability of the packaged food is increased. However, it is also possible to flush the atmosphere in the package recess out of the package by using by a replacement gas, i.e., the atmosphere in the package recess can be changed without first creating a vacuum in the package recess. In addition, it is also possible to create a vacuum in the package and thereby reduce the volume of gas present there and/or to reduce the oxygen partial pressure, for example. The gas exchange/vacuum can be induced before the sealing station and/or while in it and/or before or preferably after filling the package recess with packaging material.

Before and/or after the package has been sealed, the concentration of a gas component in the atmosphere in the package is measured. For this purpose, the package has a gas concentration indicator substance which is preferably provided in the form of dots on the inside of the plastic film, i.e., on the side of the plastic film facing the atmosphere inside the package.

A gas concentration indicator substance in the sense of the present invention comprises a substance in which a chemical and/or physical property changes with the concentration of a gas, for example, oxygen. In particular, there is a change in the wavelength of the light emitted by the gas concentration indicator substance in comparison with the light used to excite it in particular. The gas concentration indicator substance is preferably excited with green light and emits red light.

According to the present invention, the concentration of the component to be measured in the atmosphere of the package is ascertained on the basis of the decay curve of the light emitted. To do so, the gas concentration indicator substance is preferably excited in pulses, and then the intensity of the emitted light is measured. The gas concentration indicator substance is especially preferably excited with a plurality of pulses, and the decay curve of the respective emitted light is recorded.

The maximum intensity and the period of time until the emitted intensity has dropped to the level 1/e, where e is the Euler number, are preferably represented by the decay curve. This period of time, which is referred to below as "TAU," is a measure of the concentration of a component, in particular of the oxygen in the atmosphere in the package. TAU is preferably determined at a plurality of different known concentrations of the substance to be measured, in particular three different concentrations, and these measurements are used to obtain an equation for concentration=f(TAU).

In this measurement, at least one temperature measurement in the area of the package is preferably taken into account. In this way, measurement errors that occur due to temperature differences between the instantaneous measurement and the calibration are avoided. The temperature of the plastic film on which the gas concentration indicator substance is provided is preferably measured.

Preferably at least one, in particular a plurality of temperature correction parameters are taken into account for the temperature correction. The correction is most especially preferably carried out on the basis of the false light model.

According to a preferred embodiment of the present invention, the temperature correction parameter(s) is (are) determined for a category of packaging film. An example of a category of packaging film would be a PE film, a PP film or an APET film.

The TAU values and/or the temperature correction parameter(s) is (are) preferably determined for a certain gas concentration indicator substance.

The TAU values and/or the temperature correction parameter(s) is (are) preferably stored in the memory of a computer unit of a packaging machine. When the film is changed, the required values can then be retrieved from the memory. Then this computer unit also contains the conversion of the TAU values measured instantaneously to a concentration, in particular an oxygen concentration. The packaging machine is preferably controlled and/or regulated by the computer unit, in particular based on the measured TAU value.

Preferably at least one certain temperature correction parameter is determined on the basis of the packaging film currently being used. When the film is replaced, the properties of the film currently being used can also be taken into account within a certain generic type of film.

The present invention is explained below on the basis of the figures. These explanations are given merely as an example and do not restrict the general scope of the idea on which the present invention is based. These explanations apply equally to all subject matters of the present invention.

FIG. 8 shows the calibration parameters τ, $K_{SV}$, f as a function of temperature.

Figure 1:
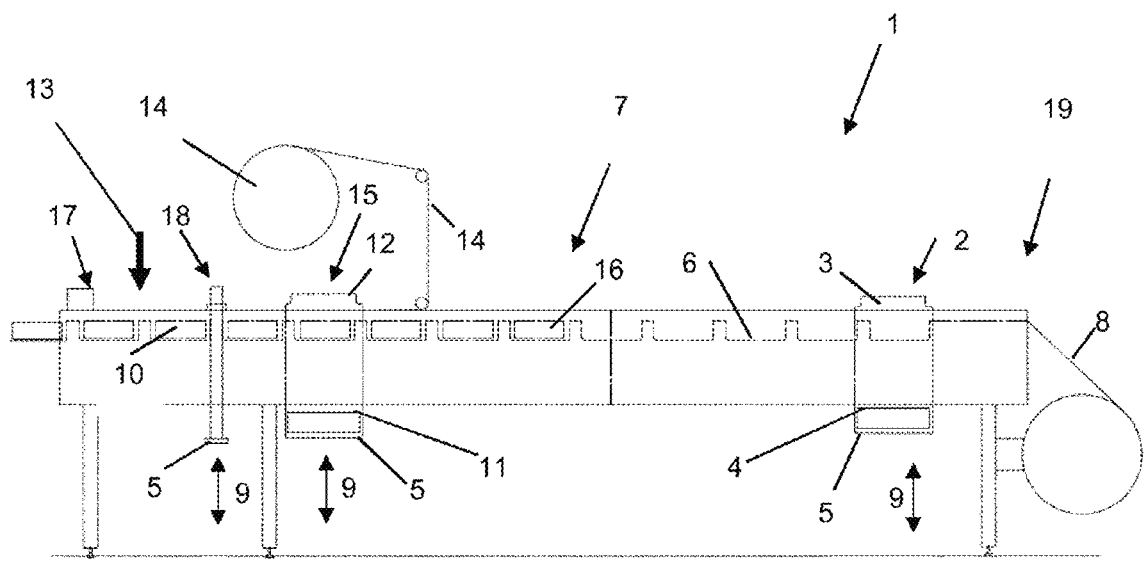
FIG. 1 shows the packaging machine according to the invention.

FIG. 1 shows a packaging machine 1, comprising a deep drawing station 2, a filling station 7 and a sealing station 15. A plastic film sheet 8, the so-called bottom film sheet, is pulled out from a supply roll, in this case from right to left, and conveyed along the packaging machine according to the invention, preferably in cycles. In one cycle, the film sheet is conveyed further by one format length. For this purpose, the packaging machine has two transport means (not shown), namely two continuous chains in the present case, provided on the right and left of the film sheet. Each continuous chain has holding means, each working together with an edge of the film sheet. At least one gear wheel about which the respective chain is deflected is provided at the beginning and at the end of the packaging machine for each chain. At least one of these gear wheels is driven. The gear wheels in the intake region 19 and/or in the outlet region may be connected to one another, preferably by a rigid shaft. Each transport means has a plurality of clamping means, which grip the bottom film sheet 8 with a clamping effect in the inlet region and transfer the movement of the transport means to the bottom film sheet 8. In the outlet region of the packaging machine, the clamping connection between the transport means and the bottom film sheet is released. The package recesses 6 are molded in the bottom film sheet 8 in the deep-drawing station 2, which has a top die 3 and a bottom die 4, the latter being in the shape of the package recess to be produced. The bottom die 4 is arranged on a lifting table 5, which is vertically adjustable, as represented by the double arrow. Before each film advancement, the bottom die 4 is lowered and then raised again. In the remaining course of the packaging machine, the package recesses are then filled with the packaging material 16 in the filling station 7. A top film sheet is sealed onto the package recess in the following sealing station 15, which also consists of a top die 12 and a vertically adjustable bottom die 11. The top die and/or the bottom die are also raised and/or lowered before and after each time the film is transported in the sealing station. The top film sheet 14 may be deep drawn and/or may be guided in the transport means and/or may be transported by the transport chains, wherein these transport means then extend only from the sealing station and optionally downstream. Otherwise the embodiments utilized for the transport means of the bottom film sheet are applicable. A gas exchange is preferably carried out in the sealing station in order to reduce the oxygen content of the atmosphere in the package, for example. In the remaining course of the packaging machine, the completed packages are also separated, which is accomplished with the cutting tool 17, 18. The cutting tool 18 can also be raised and/or lowered with a lifting device 9 in the present case. Those skilled in the art will recognize that one cycle preferably includes deep drawing, filling and sealing a plurality of package recesses.

The packaging machine has at least one measurement device, for example, a sensor 13, which reads out a spot comprising a gas concentration indicator substance inside the package and thereby reads out the concentration, for example, the oxygen concentration in the package.

The packaging machine may also have a pressure station, with which the package is preferably put under pressure, and if there are any leaks in the package, it will breathe at this point and/or its deformation and/or reformation behavior will change. This change is detected and analyzed in the pressure station itself or with a sensor downstream from it. The leaking "bad package" are sorted out.

Figure 2:
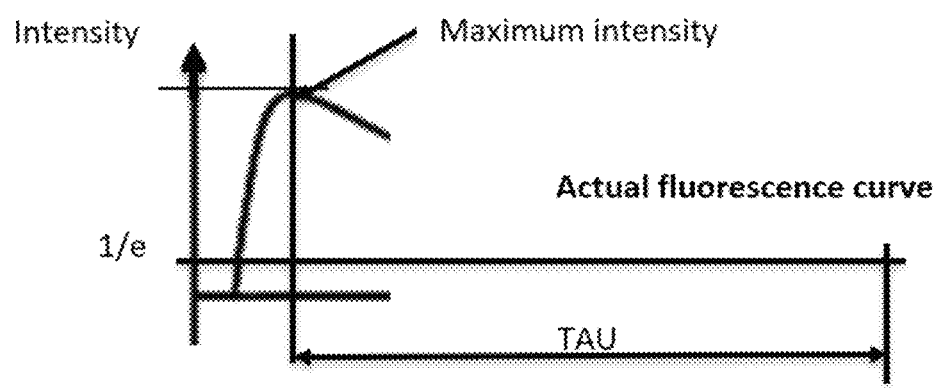
FIG. 2 shows a typical decay curve.

FIG. 2 shows a typical decay curve for light emission by a gas concentration indicator substance, comprising a fluorophor which is excited with a light pulse in the present case. The fluorophor in the gas concentration indicator substance then emits red light as a result of excitation, preferably excitation with green light, and the intensity of the red light decays over time. This light is received by the sensor, whereupon the intensity change in this light is subject to an exponential decay curve. The rate of this decay—the lifetime of the red light is used for calculating the $O_2$ concentration. To do so, the lifetime of the emission is measured as the so-called decay time TAU of the intensity of the fluorescent light, namely the red light here. Tau is defined as the period of time after which the intensity has dropped to the value 1/e. The variable TAU is the primary measurement result and is a measure of the $O_2$ concentration.

Figure 3:
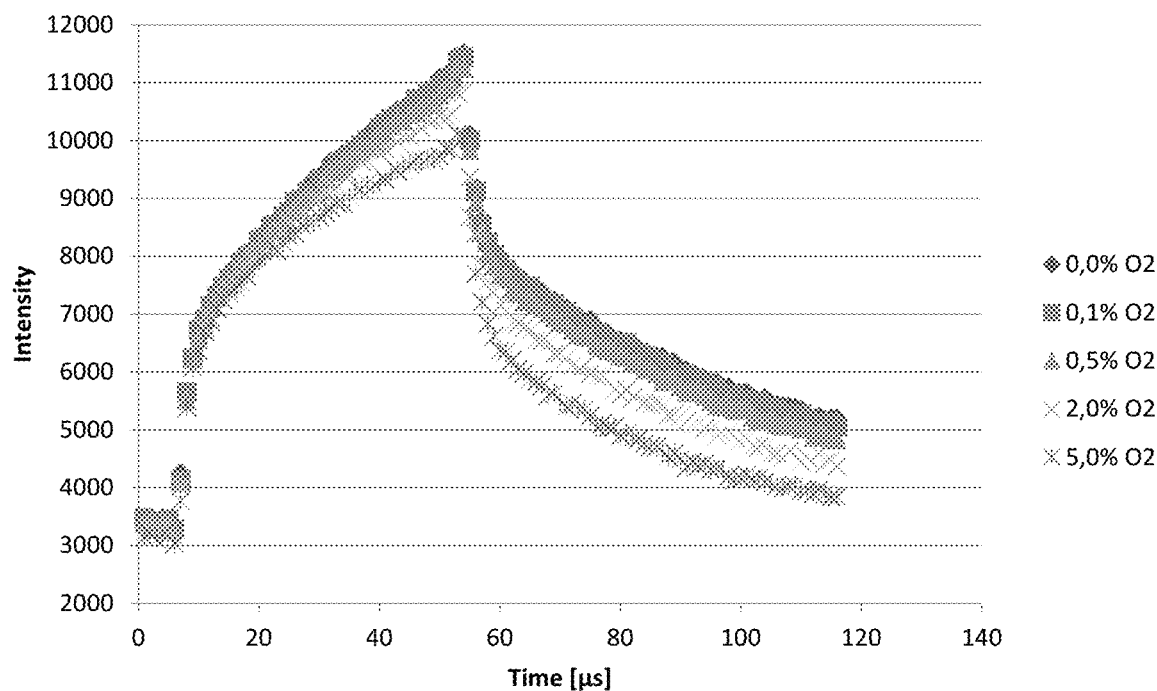
FIG. 3 shows typical measured values at different $O_2$ concentrations.
Figure 4:
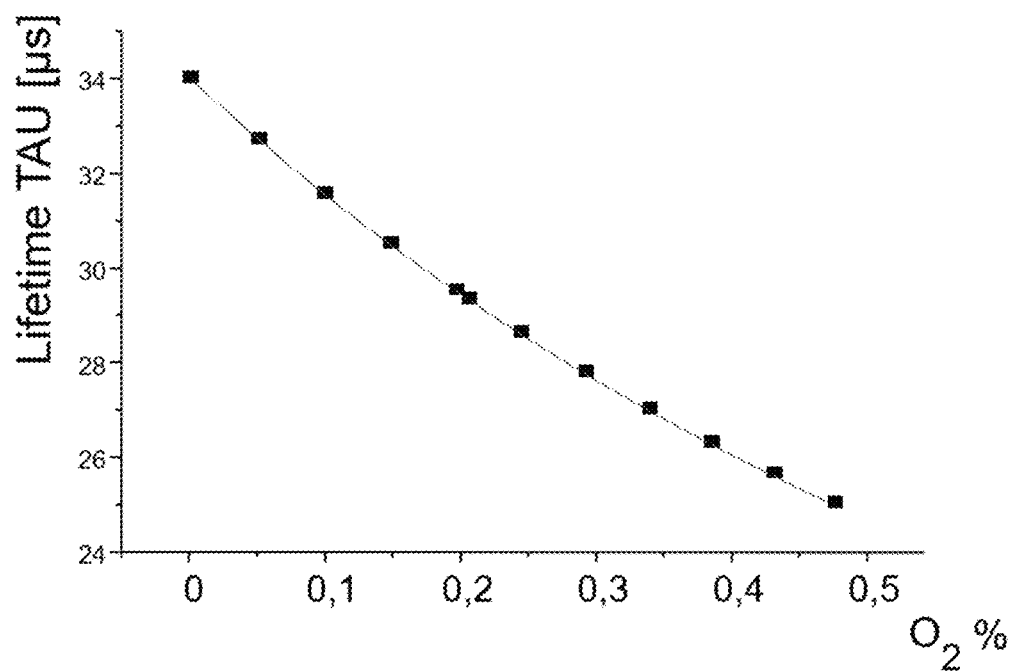
FIG. 4 shows the influence of the gas content on TAU, namely the $O_2$ content on TAU here.

FIG. 3 shows the decay curves according to FIG. 2 for five different gas concentrations, specifically oxygen concentrations here. The curve shown in FIG. 4 can be generated from these curves and those skilled in the art will recognize that different measured values were used for the curve according to FIG. 4. For this curve it is possible to determine a function, which is then stored in the computer of a packaging machine for example, and on the basis of which the gas concentration, i.e., the oxygen concentration in the package here, can be ascertained on the basis of this curve.

Those skilled in the art will recognize that the measured values may be specific for each type of film, for example, the passage of light through the film can be influenced by the optical properties of the film and then must be determined for different types of film.

The following figures relate to temperature compensation. It has surprisingly been found that the decay curves shown in FIG. 6 represent a function of the temperature of the gas concentration indicator substance, and that this is preferably to be taken into account in determination of a gas concentration in the atmosphere of a package.

Figure 5:
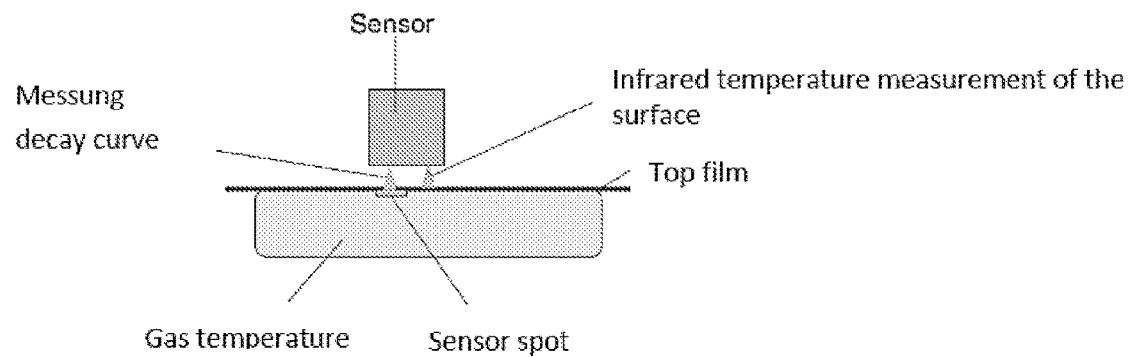
FIG. 5 shows a possible embodiment of a temperature measurement.

Therefore, FIG. 5 shows a measurement setup that is preferably to be used. It has one or more sensors, which, first, record the decay curve of the emitted light in order to be able to calculate TAU and, second have a temperature sensor, namely an infrared sensor here, to measure the temperature of the gas concentration indicator substance. However, this measurement is influenced by the temperature of the film to which the indicator substance is attached, so the temperature of this film is preferably also measured, and it is assumed in first approximation that the gas concentration indicator substance has the same temperature.

Figure 6:
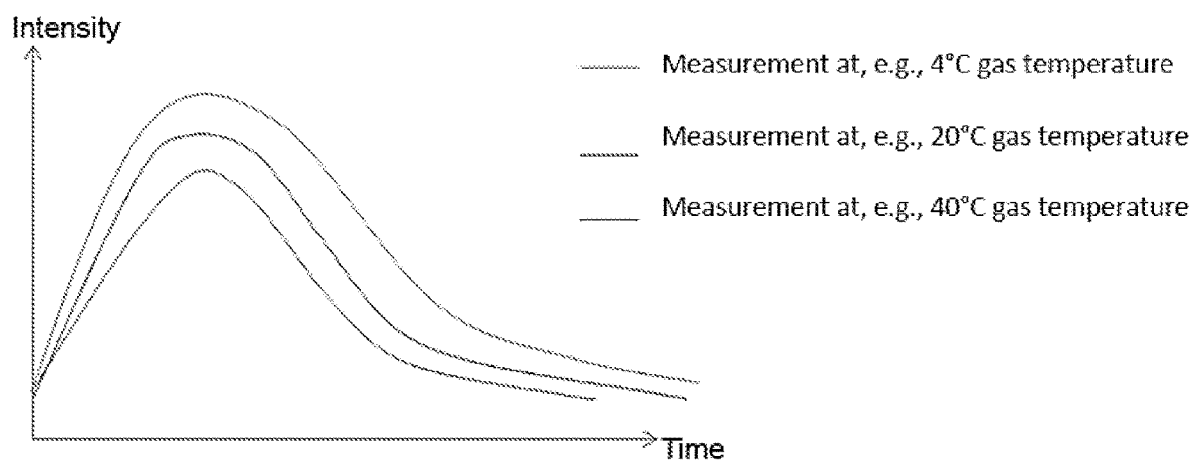
FIG. 6 shows the influence of temperature on the decay curve at a constant pressure.
Figure 7:
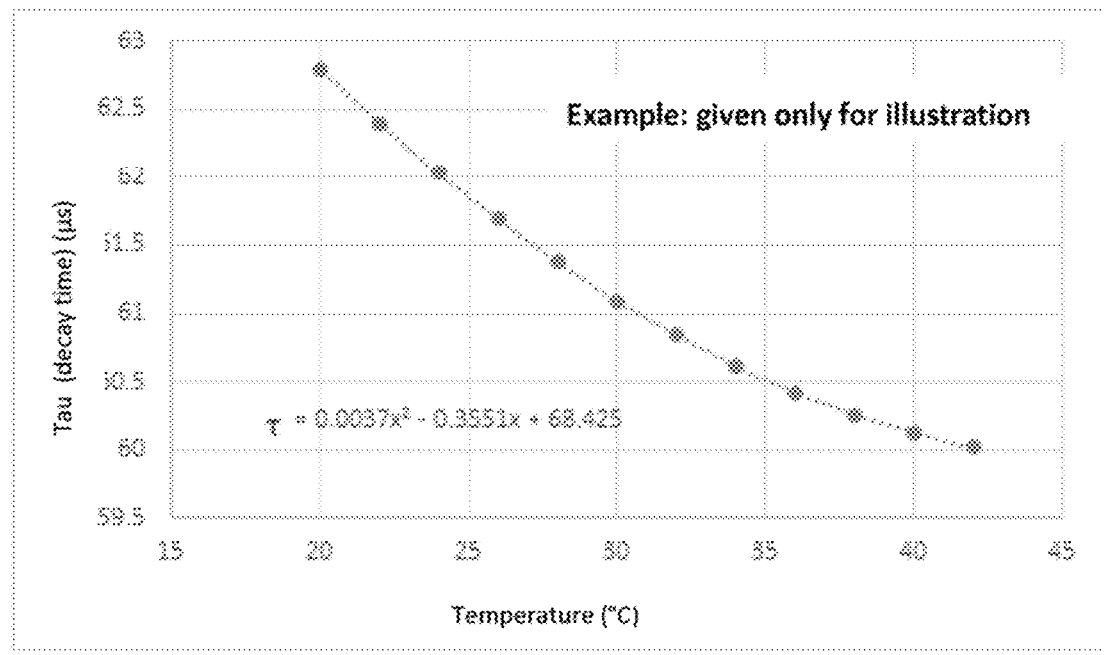
FIG. 7 shows the temperature dependence of TAU.

From the curves obtained in FIG. 6, the curve shown in FIG. 7 for a certain concentration of the component to be determined can be derived. The curve or the concentration can be correlated with the function illustrated.

The temperature compensation of measured TAU values can now be explained as follows:

The decay curves are recorded for a plurality of different concentrations, preferably five to seven different concentrations, in particular the O₂ concentrations as a function of time and temperature, i.e., per temperature, for example, all the curves according to FIG. 3. And TAU is determined for each curve, after which the temperature dependence of the TAU values can be derived and then used for the following determination of the O₂ concentration. The calibration parameters are preferably determined for each film.

These calibration parameters are input into the control unit of the packaging machine when changing the film, and the O₂ concentration values corrected for temperature are determined in this way.

For example, FIG. 8 shows a set of these nine parameters. The gas concentration, namely the O₂ concentration here, is determined on the basis of the false light model, where three parameters $\tau$, $K_{SV}$, f represent the O₂ dependence and the a, b, c indexing describes the temperature dependence.

False Light Model:

$$[O_2] = \frac{\tau_0 - \tau}{K_{SV} * \tau + K_{SV} * \tau_0 * (f - 1)}$$

$\tau$ here is TAU and is measured
$\tau_0$ is TAU 0 and is a calibration parameter
f is the radius of curvature at high O₂ concentrations
$K_{SV}$ is the curvature parameter at average O₂ concentrations FIG. 8 shows the measured temperature dependence of the calibration parameters ascertained on the basis of the equations that are also shown.

Example of the 0 Point Adjustment for a New Roll of Film

On the basis of a curve analysis, the temperature dependence of the parameter TAU 0 with which the function TAU is described at dropping temperatures is determined. FIG. 7 illustrates an example of a TAU function. The TAU 0 values determined for the film replace the values for TAU 0 previously determined for the film in a laboratory, for example. To do so, the following procedure is followed on the packaging machine:

1) A package with approximately 0% O₂ content is generated with the "step vacuum" function in the sealing station. One and the same preference//? and subsequent regassing with O₂-free N₂ or CO₂/N₂ mixture can be performed by evacuating three times. The resulting reference package (null package) has the lowest possible residual oxygen content, and an O₂ content of 0% is assumed for the sake of simplicity.

2) Initially the package is very warm but it cools down according to its own cooling curve. In doing so, many value parameters of temperature and TAU are measured and recorded. This yields the exact cooling curve according to FIG. 7, which represents the temperature dependence of the TAU value (decay time/lifetime).

3) The calibration parameter $T_0$ is determined from this (the temperature dependence is represented by $T_0$, $T_{0b}$ and $T_{0c}$). This is used for film-specific calculation of the O₂ concentration by the machine control unit.

4) Next, the actual packages are produced and, more or less at the same time, the intensity is measured as a function of time and temperature (about 10 times). Then TAU values are determined from this, and the average TAU values and the temperature value are sent to the machine control unit.

5) The average TAU values are converted by the machine control unit into O₂ values using the false light model with the help of the temperature-dependent parameters, which are determined as described above (see FIG. 8).

In this way, a value for the O₂ concentration that has been corrected with regard to temperature is obtained for each sensor spot and/or for each package.

Example of the Sequence of Temperature Compensation:

1) The temperature-dependent calibration parameters are determined for each film on a test stand by determining the temperature dependence at three temperatures with a constant O₂ concentration.

2) The temperature dependence of the calibration parameters TAU 0, $K_{SV}$ and f is determined from the data thereby obtained.

Example of the Sequence of 0 Point Adjustment:

1) Null packages are produced on the packaging machine.
2) The temperature of the film is equated with the temperature of the sensor spot for the sake of simplicity, amounting to 42° C. at the moment of the first measurement, for example.
3) The TAU values are determined as a function of temperature, and the calibration parameter TAU 0 is calculated from this.
4) The measured data yield the values for TAU=65 and T=42° C., for example.
5) The preceding curve analysis yields the three calibration parameters TAU 0=67, $K_{SV}$=0.25 and f=0.75.

$O_2 = (67-65)/(0.25*65+0.25*67*(0.75-1)) = 0.185\%$

LIST OF REFERENCE NUMERALS

1 Packaging machine
2 Deep-drawing station
3 Top die of the deep drawing station
4 Bottom die of the deep drawing station
5 Lifting table, support for a die in the sealing station and deep-drawing station and/or the cutting device
6 Package recess
7 Filling station
8 Bottom film sheet
9 Lifting device
10 Completed package
11 Bottom die of the sealing station
12 Top die of the sealing station
13 Sensor, oxygen sensor
14 Top film
15 Sealing station
16 Packaging material
17 Longitudinal cutting device
18 Transverse cutting device
19 Inlet region

The invention claimed is:

1. A method for measuring a concentration of a gas component in an atmosphere of a package, the package being produced from a plastic film in a packaging machine, the package has a gas concentration indicator substance on a side of the plastic film facing the atmosphere,
wherein the gas concentration indicator substance is exposed to an electromagnetic radiation of a wavelength, the gas concentration indicator substance is excited with a plurality of pulses, which then emits light at a different wavelength than the wavelength of the electromagnetic radiation, and the concentration of the gas is determined on a basis of a decay curve of the emitted light, and wherein at least one temperature correction parameter is determined for a category of the plastic film that is made of a particular material, the determined at least one temperature correction parameter is stored in a memory of a computer of the packaging machine, and the determined at least one temperature correction parameter is retrieved from the memory when the plastic film is replaced in the packaging machine, the determined at least one temperature correction parameter that is stored in the memory includes a temperature measurement of the plastic film, and the temperature measurement of the plastic film that is stored in the memory and then retrieved from the memory is utilized in determining the concentration of the gas component, wherein the method comprises:
i) generating a reference package;
ii) measuring and recording one or more temperature parameters of the reference package during cooling of the reference package to determine a cooling curve of the reference package; and
iii) determining the at least one temperature correction parameter from the cooling curve of the reference package.

2. The method according to claim 1, wherein a temperature of the plastic film to which the gas concentration indicator substance is attached is measured.

3. The method according to claim 1, wherein the at least one temperature correction parameter is performed on a basis of a false light model for determining the gas concentration.

4. The method according to claim 1, wherein the at least one temperature correction parameter is determined for a certain gas concentration indicator substance.

5. The method according to claim 1, wherein a certain temperature correction parameter is determined on the packaging plastic film currently in use.

6. The method according to claim 1, wherein the gas concentration indicator substance is excited with a green light and emits a red light.

7. The method according to claim 1, wherein fluorophor in the gas concentration indicator substance emits a red light, and an intensity of the red light decays over time.

8. The method according to claim 1, wherein the category of the film is polyethylene plastic film, polypropylene film, or an amorphous polyethylene terephthalate film.

9. A method for measuring a concentration of a gas component in an atmosphere of a package, which is produced from a plastic film in a packaging machine and has a gas concentration indicator substance on a side the plastic film facing the atmosphere, wherein the gas concentration indicator substance is exposed to an electromagnetic radiation of a wavelength, the gas concentration indicator substance is excited with a plurality of pulses, which then emits light at a different wavelength than the wavelength of the electromagnetic radiation, and the gas concentration is determined on a basis of a decay curve of the emitted light, wherein at least one temperature correction parameter is determined for a category of the plastic film, the category of the plastic film is polyethylene film, polypropylene film, or an amorphous polyethylene terephthalate film, wherein the at least one temperature correction parameter is stored in a memory of a computer, and the at least one temperature correction parameter is retrieved from the memory during a change out of the plastic film, the at least one temperature correction parameter is utilized in determining the concentration of the gas component, wherein the at least one temperature correction parameter is determined on the plastic film currently in use, wherein fluorophor in the gas concentration indicator substance emits red light, and an intensity of the red light decays over time, and wherein a gas exchange in the packaging machine is controlled according to the measured concentration of the gas, wherein the method comprises:
i) generating a reference package;
ii) measuring and recording one or more temperature parameters of the reference package during cooling of the reference package to determine a cooling curve of the reference package; and
iii) determining the at least one temperature correction parameter from the cooling curve of the reference package.

10. The method according to claim 1, wherein the packaging machine comprises a deep drawing station, a filling station, a sealing station, and a sensor, which reads out the gas concentration indicator substance inside of the package.

11. The method according to claim 10, wherein the method comprises:
generating the package and measuring an intensity of the emitted light as a function of time and temperature, and determining the decay curve of the emitted light and sending the decay curve to the computer; and
converting with the computer, the decay curve to the gas concentration using a false light model and the at least one temperature correction parameter determined from the reference package to correct a value of the concentration of the gas component.

12. The method according to claim 11, wherein the packaging machine has a pressure station, where the package is put under pressure to test for leaks.

13. The method according to claim 11, wherein the reference package has a gas content of approximately 0%, and the method includes measuring a temperature of the gas concentration indicator substance with an infrared sensor.

14. The method according to claim 1, wherein the method comprises:
i) generating the package and measuring an intensity of the emitted light as a function of time and temperature, and determining the decay curve of the emitted light and sending the decay curve to the computer; and
ii) converting with the computer, the decay curve to the gas concentration.

15. The method according to claim 10, wherein the packaging machine has a pressure station, where the package is put under pressure to test for leaks, and wherein the reference package has a gas content of approximately 0%, and the method includes measuring a temperature of the gas concentration indicator substance with an infrared sensor.

* * * * *

UNITED STATES PATENT AND TRADEMARK OFFICE
CERTIFICATE OF CORRECTION

PATENT NO. : 11,692,984 B2
APPLICATION NO. : 16/610149
DATED : July 4, 2023
INVENTOR(S) : Andreas Steffen et al.

It is certified that error appears in the above-identified patent and that said Letters Patent is hereby corrected as shown below:

In the Claims

Column 7, Lines 40 and 41, Claim 5, delete "packaging" after "determined on the"
Column 7, Line 54, Claim 9, insert --of-- after "on a side"

Signed and Sealed this
Twenty-ninth Day of August, 2023

Katherine Kelly Vidal
*Director of the United States Patent and Trademark Office*